United States Patent [19]

Müller et al.

[11] Patent Number: 5,352,687
[45] Date of Patent: Oct. 4, 1994

[54] SUBSTITUTED PHENYLACETAMIDES

[75] Inventors: Ulrich E. Müller, Wuppertal; Matthias Müller-Gliemann, Solingen Ohligs; Jürgen Dressel; Peter Fey, both of Wuppertal; Rudolf Hanko, Duesseldorf; Walter Hübsch; Thomas Kramer, both of Wuppertal; Martin Beuck, Erkrath; Stanislav Kazda, Wuppertal; Stefan Wohlfeil, Hilden; Özkan Yalkinoglu, Wuppertal; Andreas Knorr, Erkrath; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 25,479

[22] Filed: Mar. 3, 1993

[30] Foreign Application Priority Data

Mar. 13, 1992 [DE] Fed. Rep. of Germany ....... 4208051

[51] Int. Cl.$^5$ .................. A61K 31/535; A61K 31/47; C07D 413/10; C07D 407/10
[52] U.S. Cl. .................. 514/341; 514/235.8; 514/312; 514/314; 514/397; 544/139; 546/155; 546/156; 546/157; 546/167; 546/278; 548/311.4; 548/315.1; 548/315.4
[58] Field of Search ............... 544/139; 546/278, 155, 546/156, 157, 117; 548/311.4, 315.1, 315.4; 514/235.8, 312, 314, 341, 397

[56] References Cited

U.S. PATENT DOCUMENTS 4,355,040 10/1982 Furukawa et al. ............. 424/273 R
4,946,841 8/1990 Baader et al. ..................... 514/247

FOREIGN PATENT DOCUMENTS

| | | |
|---|---|---|
| 0399731 | 11/1990 | European Pat. Off. |
| 0399732 | 11/1990 | European Pat. Off. |
| 0407102 | 1/1991 | European Pat. Off. |
| 0324377 | 2/1991 | European Pat. Off. |
| 9112002 | 8/1991 | PCT Int'l Appl. |

OTHER PUBLICATIONS

Upsekhi Khimii, Russian Chemical Reviews, 32, 1 (1963).
Frerman, et al., "Leucine Catabolism during the Differentiation of 3TG3-L1 Cells", 258, 7087-1093 (1983).
Ross, R., The Journal of Cell Biology, vol. 50, 1971, 172-186.
Benoiton, et al., Int. Pept. Prot. Res. 17, 197 (1981).
Sheehan, et al., J. Am. Chem. Soc. 95, 875 (1973).
J. Am. Chem. Soc., Chem. Comm. (2) 167-168 (1966).
Journal of Medicinal Chemistry, vol. 33, No. 5, May 1990, 1312-1329.
S. R. Adapa & C. S. N. Prasad, J. Chem. Soc., Perkin Trans. 1, (9) pp. 1706-1707 (1989).

Primary Examiner—Patricia L. Morris
Attorney, Agent, or Firm—Sprung Horn Kramer & Woods

[57] ABSTRACT

Substituted phenylacetamides can be prepared by reaction of appropriately substituted phenylacetic acids with imidazoles and subsequent amidation. The substituted phenylacetic acid derivatives can be employed in medicaments for the treatment of high blood pressure and atherosclerosis.

6 Claims, No Drawings

SUBSTITUTED PHENYLACETAMIDES

The invention relates to substituted phenylacetamides, processes for their preparation, and their use in medicaments, in particular as hypotensive and antiatherosclerotic agents.

It is known that renin, a proteolytic enzyme, cleaves the decapeptide angiotensin I, which is in turn degraded in the lungs, the kidneys or other tissues to the hypertensive octapeptide angiotensin II, from angiotensinogen in vivo. The various effects of angiotensin II, such as, for example, vasoconstriction, Na+ retention in the kidney, aldosterone release in the adrenal gland and increase in tone of the sympathetic nervous system act synergistically in the sense of an increase in blood pressure.

Moreover, angiotensin II has the property of promoting the growth and the replication of cells such as, for example, of heart muscle cells and smooth muscle cells, where these grow at an increased rate and proliferate in various disease states (for example hypertension, atherosclerosis and cardiac insufficiency).

In addition to the inhibition of renin activity, a possible starting point for intervention in the reninangiotensin system (RAS) is the inhibition of the activity of angiotensin-converting enzyme (ACE) and the blockade of angiotensin II receptors.

Moreover, heterocyclic compounds having A II-antagonistic action are known from the publications EP 407,102, EP 399,731; EP 399,732 and EP 324,347.

The invention relates to substituted phenylacetamides of the general formula (I)

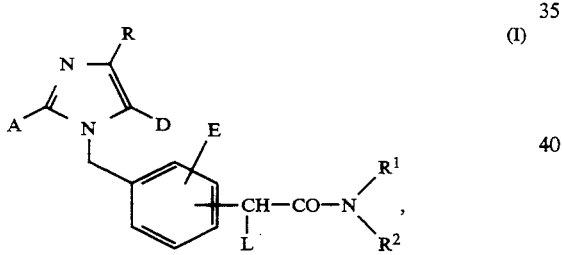

in which
A represents straight-chain or branched alkyl or alkenyl each having up to 8 carbon atoms, or represents cycloalkyl having 3 to 8 carbon atoms,
B represents hydrogen, halogen or perfluoroalkyl having up to 5 carbon atoms,
D represents a group of the formula $-CH_2OR^3$, $-CO-R^4$, $-CO-NR^5R^6$,

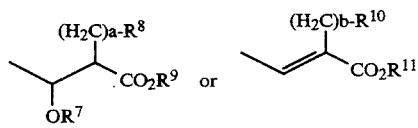

in which
$R^3$ denotes hydrogen or straight-chain or branched alkyl having up to 8 carbon atoms,
$R^4$ represents hydrogen, hydroxyl or straight-chain or branched alkoxy having up to 8 carbon atoms,
$R^5$ and $R^6$ are identical or different and denote hydrogen, straight-chain or branched alkyl having up to 8 carbon atoms, or $R^5$ has the abovementioned meaning and
$R^6$ denotes a group of the formula $-SO_2R^{12}$, in which
$R^{12}$ denotes straight-chain or branched alkyl having up to 6 carbon atoms, or benzyl or phenyl which are optionally substituted by straight-chain or branched alkyl having up to 6 carbon atoms,
a and b are identical or different and denote a number 0, 1 or 2,
$R^7$ denotes hydrogen or straight-chain or branched alkyl having up to 8 carbon atoms or a hydroxyl protective group,
$R^8$ and $R^{10}$ are identical or different and denote hydrogen, straight-chain or branched alkyl having up to 6 carbon atoms, cycloalkyl having 3 to 8 carbon atoms, phenyl or thienyl,
$R^9$ and $R^{11}$ are identical or different and denote hydrogen or straight-chain or branched alkyl having up to 8 carbon atoms,
E represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl,
L represents straight-chain or branched alkyl having up to 8 carbon atoms, which is optionally substituted by cycloalkyl having 3 to 8 carbon atoms or by phenyl, represents cycloalkyl having 3 to 12 carbon atoms, which is optionally substituted by straight-chain or branched alkyl having up to 6 carbon atoms,
$R^1$ represents hydrogen or straight-chain or branched alkyl having up to 8 carbon atoms,
$R^2$, with the exception of tetrazolyl, represents a 5- to 7-membered, saturated or unsaturated heterocycle or a benzo-fused heterocycle bonded via phenyl and having up to 3 heteroatoms from the series consisting of S, N and O, which are optionally substituted up to 3 times by identical or different substituents from the group consisting of nitro, cyano, halogen, hydroxyl, trifluoromethyl, carboxyl, straight-chain or branched alkoxy or alkoxycarbonyl each having up to 6 carbon atoms, phenoxy, benzyloxy, phenoxycarbonyl and benzyloxycarbonyl, or represents a radical of the formula

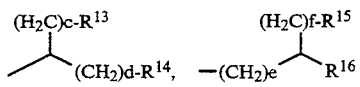

or

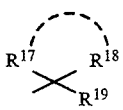

in which
$R^{13}$ denotes phenyl which is optionally substituted up to 3 times by identical or different substituents from the group consisting of halogen, hydroxyl and trifluoromethyl or by straight-chain or branched alkyl or alkoxy each having up to 8 carbon atoms,
c, d, e and f are identical or different and denote a number 0, 1, 2, 3 or 4,
$R^{14}$ denotes hydrogen, trifluoromethyl, carboxyl or straight-chain or branched alkoxycarbonyl having up to 8 carbon atoms, or the group $-CO-NH_2$, or a 5- to 7-membered, saturated or unsaturated heterocycle having up to 3 heteroatoms from the series consisting of S, N and O, $R^{15}$ denotes cycloalkyl having 3 to 8 carbon atoms or benzo[b]dioxolyl, $R^{17}$ and $R^{18}$ together form a saturated carbocycle having 3 to 8 carbon atoms, $R^{16}$ and $R^{19}$ are identical or different and denote trifluoromethyl or straight-chain or branched alkyl having up to 8 carbon atoms, which is optionally substituted up to 3 times by identical or different substituents from the group consisting of hydroxyl, carboxyl, trifluoromethyl, halogen, nitro and cyano, by straight-chain or branched alkoxy, acyl or alkoxycarbonyl each having up to 8 carbon atoms or by phenyl or a 5- to 7-membered, saturated or unsaturated heterocycle having up to 3 heteroatoms from the series consisting of S, N and O, which can in turn be substituted up to 2 times by identical or different halogen, nitro, cyano or hydroxyl substituents or by straight-chain or branched alkyl or alkoxy each having up to 6 carbon atoms, or alkyl is optionally substituted by a group of the formula —CO—$NR^{20}R^{21}$, in which $R^{20}$ and $R^{21}$ have the abovementioned meaning of $R^5$ and $R^6$ and are identical to or different from these, or $R^{20}$ and $R^{21}$, together with the nitrogen atom, form a 5- to 7-membered, saturated or unsaturated heterocycle having up to 2 further heteroatoms from the series consisting of S, N and O, or $R^{16}$ and/or $R^{19}$ denote straight-chain or branched alkoxy or alkoxycarbonyl each having up to 8 carbon atoms, hydroxyl, carboxyl or the group of the formula —CO—$NR^{20}R^{21}$, in which $R^{20}$ and $R^{21}$ have the abovementioned meaning, or $R^1$ and $R^2$, together with the nitrogen atom, form a 5- to 7-membered, saturated or unsaturated heterocycle having up to 2 further heteroatoms from the series consisting of S, N and O and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the heterocyclically substituted phenylacetic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which behave either as image and mirror image (enantiomers) or which do not behave as image and mirror image (diastereomers). The invention relates both to the enantiomers or diastereomers or their respective mixtures. The racemic forms can be resolved into the stereoisomerically uniform constituents in a known manner just like the diastereomers [cf. E. L. Eliel, Stereochemistry of Carbon Compounds, McGraw Hill, 1962].

Heterocycle or benzo-fused heterocycle in general represents a 5- to 7-membered, preferably 5- to 6-membered, saturated or unsaturated ring which as heteroatoms can contain up to 2 oxygen, sulphur and/or nitrogen atoms. 5- and 6-membered rings having an oxygen, sulphur and/or up to 2 nitrogen atoms are preferred. The following are mentioned as preferred: thienyl, furyl, pyrrolyl, pyrazolyl, pyridyl, quinolinyl, tetrahydrofuranyl, tetrahydropyranyl, dihydrobenzapyranyl, dihydrobenzofuranyl or benzo[b]dioxolyl . Pyridyl, furanyl, thienyl tetrahydrofuranyl, pyrrolidinyl or benzo[b]dioxyl are particularly preferred.

Hydroxyl protective group, in the context of the abovementioned definition, represents a protective group from the series consisting of: trimethylsilyl, triethylsilyl, triisopropylsilyl, tert-butyldiphenylsilyl, tert-butyldiphenylsilyl, trimethylsilylethoxycarbonyl, benzyl, triphenylmethyl(trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl or 4-methoxybenzoyl. Acetyl is preferred.

Preferred compounds of the general formula (I) are those in which

A represents straight-chain or branched alkyl or alkenyl each having up to 6 carbon atoms, or represents cyclopropyl, cyclobutyl, cyclopentyl, cyclohexyl or cycloheptyl, R represents hydrogen, fluorine, chlorine, bromine or perfluoroalkyl having up to 4 carbon atoms, D represents a group of the formula —$CH_2OR^3$, —CO—$R^4$, —CO—$NR^5R^6$,

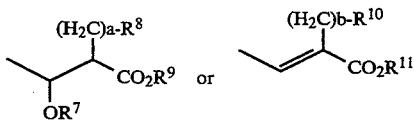

in which $R^3$ denotes hydrogen or straight-chain or branched alkyl having up to 6 carbon atoms, $R^4$ denotes hydrogen, hydroxyl or straight-chain or branched alkoxy having up to 6 carbon atoms, $R^5$ and $R^6$ are identical or different and denote hydrogen or straight-chain or branched alkyl having up to 6 carbon atoms, or $R^5$ has the abovementioned meaning and $R^6$ denotes a group of the formula —$SO_2R^{12}$, in which $R^{12}$ denotes straight-chain or branched alkyl having up to 4 carbon atoms, or benzyl or phenyl which are optionally substituted by straight-chain or branched alkyl having up to 4 carbon atoms, a and b are identical or different and denote a number 0 or 1, $R^7$ denotes hydrogen or straight-chain or branched alkyl having up to 6 carbon atoms or acetyl, $R^8$ and $R^{10}$ are identical or different and denote straight-chain or branched alkyl having up to 4 carbon atoms, cyclopropyl, cyclobutyl, cyclopentyl, cyclohexyl or cycloheptyl, phenyl or thienyl, $R^9$ and $R^{11}$ are identical or different and denote hydrogen or straight-chain or branched alkyl having up to 6 carbon atoms, E represents hydrogen, fluorine, chlorine, bromine, trifluoromethyl, carboxyl or straight-chain or branched alkyl, alkoxy or alkoxycarbonyl each having up to 4 carbon atoms, L represents straight-chain or branched alkyl having up to 6 carbon atoms, which is optionally substituted by cyclopropyl, cyclobutyl, cyclopentyl, cyclohexyl, cycloheptyl, cyclooctyl or phenyl, represents cyclopropyl, cyclobutyl, cyclopentyl, cyclohexyl, cycloheptyl or cyclooctyl which are optionally substituted by straight-chain or branched alkyl having up to 4 carbon atoms, $R^1$ represents hydrogen or straight-chain or branched alkyl having up to 6 carbon atoms, $R^2$ represents pyridyl, morpholinyl, tetrahydropyranyl, tetrahydrofuranyl, quinolinyl, dihydrobenzopyranyl or dihydrobenzofuranyl which are optionally substituted up to 2 times by identical or different substituents from the group consisting of nitro, cyano, fluorine, chlorine, bromine, hydroxyl, straight-chain or branched alkoxy having up to 4 carbon atoms, phenoxy and benzyloxy, or represents a radical of the formula

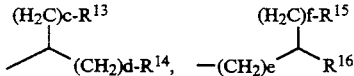

or

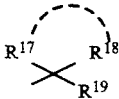

in which $R^{13}$ denotes phenyl which is optionally substituted up to 2 times by identical or different substituents from the group consisting of fluorine, chlorine, bromine, hydroxyl and trifluoromethyl or by straight-chain or branched alkyl or alkoxy each having up to 6 carbon atoms, c, d, e and f are identical or different and denote a number 0, 1, 2 or 3, $R^{14}$ denotes hydrogen, trifluoromethyl, carboxyl or straight-chain or branched alkoxycarbonyl having up to 6 carbon atoms, or the group $-CO-NH_2$, pyridyl or morpholinyl, $R^{15}$ denotes cyclopropyl, cyclobutyl, cyclopentyl, cyclohexyl, cycloheptyl or benzo[b]dioxolyl, $R^{17}$ and $R^{18}$ together form a cyclopentyl or cyclohexyl ring, $R^{16}$ and $R^{19}$ are identical or different and denote trifluoromethyl or straight-chain or branched alkyl having up to 6 carbon atoms, which is optionally substituted up to 2 times by identical or different substituents from the series consisting of hydroxyl, carboxyl, trifluoromethyl, fluorine, chlorine and bromine, by straight-chain or branched alkoxy, acyl or alkoxycarbonyl each having up to 6 carbon atoms or by phenyl, pyridyl, tetrahydrofuranyl, tetrahydropyranyl, quinolinyl, dihydrobenzopyranyl or dihydrobenzofuranyl, where the latter can optionally be substituted by fluorine, chlorine or hydroxyl, or alkyl can optionally be substituted by a group of the formula $-CO-NR^{20}R^{21}$, in which $R^{20}$ and $R^{21}$ have the abovementioned meaning of $R^5$ and $R^6$ and are identical to or different from these, or $R^{20}$ and $R^{21}$, together with the nitrogen atom, form a morpholine ring, or $R^{16}$ and/or $R^{19}$ denote straight-chain or branched alkoxy or alkoxycarbonyl each having up to 6 carbon atoms, hydroxyl, carboxyl or the group of the formula $-CO-NR^{20}R^{21}$, in which $R^{20}$ and $R^{21}$ have the abovementioned meaning, or $R^1$ and $R^2$, together with the nitrogen atom, form a morpholine or piperidine ring and their salts.

Particularly preferred compounds of the general formula (I) are those in which

A represents straight-chain or branched alkyl or alkenyl each having up to 4 carbon atoms, or represents cyclopropyl, cyclopentyl or cyclohexyl, R represents hydrogen, fluorine, chlorine or perfluoroalkyl having up to 2 carbon atoms, D represents a group of the formula $-CH_2OR^3$, $-CO-R^4$, $-CO-NR^5R^6$,

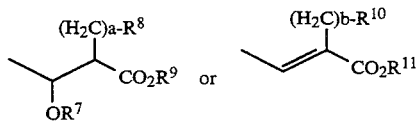

in which $R^3$ denotes hydrogen or straight-chain or branched alkyl having up to 4 carbon atoms, $R^4$ denotes hydrogen, hydroxyl or straight-chain or branched alkoxy having up to 4 carbon atoms, $R^5$ and $R^6$ are identical or different and denote hydrogen or straight-chain or branched alkyl having up to 4 carbon atoms, or $R^5$ has the abovementioned meaning and $R^6$ denotes a group of the formula $-SO_2R^{12}$, in which $R^{12}$ denotes methyl, ethyl, benzyl, p-tolyl or phenyl, a and b are identical or different and denote a number 0 or 1, $R^7$ denotes hydrogen or straight-chain or branched alkyl having up to 4 carbon atoms, $R^8$ and $R^{10}$ are identical or different and denote cyclopropyl, cyclohexyl or phenyl, $R^9$ and $R^{11}$ are identical or different and denote hydrogen or straight-chain or branched alkyl having up to 4 carbon atoms, E represents hydrogen, fluorine, chlorine, bromine, trifluoromethyl, trifluoromethoxy or methyl, L represents straight-chain or branched alkyl having up to 4 carbon atoms, which is optionally substituted by cyclopropyl, cyclopentyl, cyclohexyl, cycloheptyl or phenyl, represents cyclopropyl, cyclopentyl, cyclohexyl, cycloheptyl or cyclooctyl, $R^1$ represents hydrogen or straight-chain or branched alkyl having up to 4 carbon atoms, $R^2$ represents pyridyl, morpholinyl, tetrahydropyranyl or tetrahydrofuranyl, or represents a radical of the formula

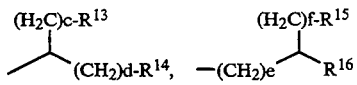

or

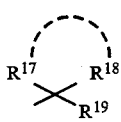

in which $R^{13}$ denotes phenyl which is optionally substituted by fluorine, hydroxyl, trifluoromethyl or by straight-chain or branched alkyl or alkoxy each having up to 4 carbon atoms, c, d, e and f are identical or different and denote a number 0, 1 or 2, $R^{14}$ denotes hydrogen, trifluoromethyl, carboxyl or straight-chain or branched alkoxycarbonyl having up to 4 carbon atoms, or the group —CO—NH$_2$, or pyridyl, $R^{15}$ denotes cyclopentyl, cyclohexyl or benzo[b]-dioxolyl, $R^{17}$ and $R^{18}$ together form a cyclopentyl or cyclohexyl ring, $R^{16}$ and $R^{19}$ are identical or different and denote trifluoromethyl or straight-chain or branched alkyl having up to 4 carbon atoms, which is optionally substituted by hydroxyl, carboxyl, trifluoromethyl, straight-chain or branched alkoxy, acyl or alkoxycarbonyl each having up to 4 carbon atoms, or by the group —CO—NH$_2$, or by phenyl or pyridyl, or denotes straight-chain or branched alkoxy or alkoxycarbonyl each having up to 4 carbon atoms, hydroxyl or carboxyl and their salts.

Moreover, a process for the preparation of the compounds of the general formula (I) according to the invention was found, which is characterised in that compounds of the general formula (II)

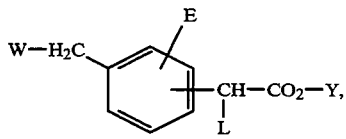

in which

E and L have the abovementioned meaning

W represents a typical leaving group such as, for example, chlorine, bromine, iodine, tosylate or mesylate, preferably bromine, and Y represents $C_1$–$C_6$-alkyl, are first reacted with imidazoles of the general formula (III)

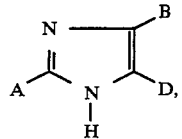

in which

A, B and D have the abovementioned meaning, in inert solvents, if appropriate in the presence of a base and if appropriate under a protective gas atmosphere, to give compounds of the general formula (IV)

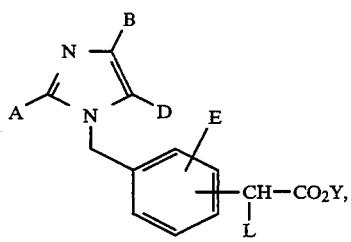

in which

A, B, D, E, L and Z have the abovementioned meaning, and, if appropriate after prior hydrolysis and/or activation, are then amidated with amines of the general formula (V)

$HNR^1R^2$ (V)

in which $R^1$ and $R^2$ have the abovementioned meaning, if appropriate in the presence of a base and/or of an auxiliary, for example a dehydrating agent, in inert solvents, and if appropriate the substituents A, B, D and E are introduced by customary methods, for example by reduction, oxidation, alkylation or hydrolysis or converted into other groups and if appropriate the isomers are separated, and in the case of the preparation of the salts reacted with an appropriate base or acid.

The process according to the invention can be illustrated by way of example by the following equation:

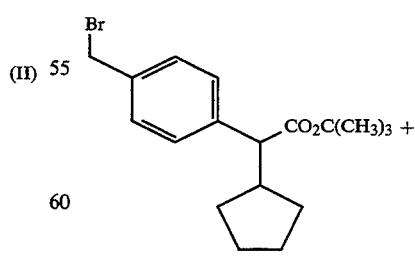

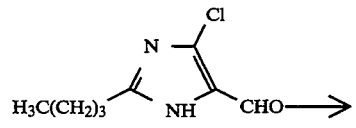

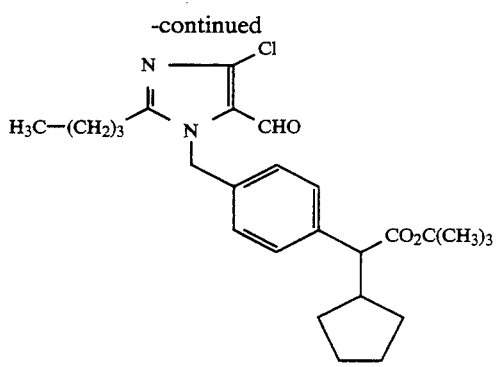

1) Trifluoroacetic acid
2) Triethylamine/methanesulphonyl chloride
3) DMAP

Suitable solvents for the process are customary organic solvents which do not change under the reaction conditions. These preferably include ethers such as diethyl ether, dioxane, tetrahydrofuran or glycol dimethyl ether, or hydrocarbons such as benzene, toluene, xylene, hexane, cyclohexane or mineral oil fracions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Dimethylformamide and tetrahydrofuran are preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium or its hydrides such as sodium hydride, as bases. Sodium hydride, potassium carbonate, triethylamine, pyridine and potassium tert-butoxide, DBU or DABCO are preferred.

In general, the base is employed in an amount from 0.05 mol to 10 mol, preferably from 1 mol to 2 mol, relative to 1 mol of the compound of the formula (III).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogencarbonate, or alkali metal alkoxides such as sodium methoxide, sodium ethoxide, potassium methoxide, potassium ethoxide or potassium tert-butoxide. Lithium hydroxide, sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

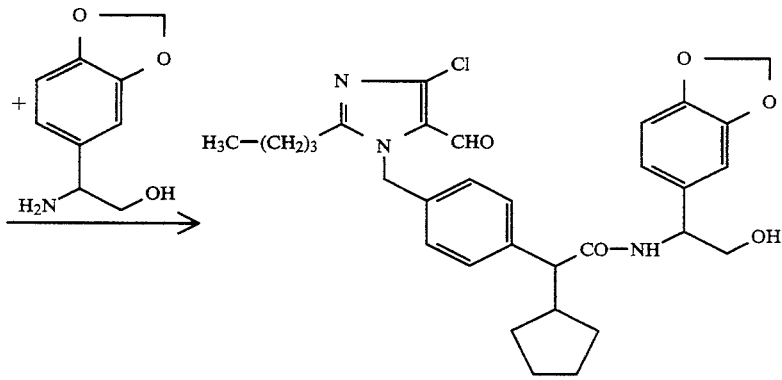

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has proved advantageous in this case in the preparation of the carboxylic acids to acidify the basic reaction mixture from the hydrolysis in a second step without isolation of the carboxylates. The acids can then be isolated in a customary manner. In the case of the basic heterocycles, the salts of the heterocycles with the inorganic acids can also be obtained by treating the solutions of the carboxylates with the abovementioned acids.

The amidation of the compounds of the general formula (IV) is in general carried out in one of the abovementioned solvents, preferably in tetrahydrofuran or dichloromethane.

The amidation may optionally proceed via the activated step of the acid halides [(IV) Y=halogen], which can be prepared from the corresponding acids by reaction with thionyl chloride, phosphorus trichloride, phosphorus pentachloride, phosphorus tribromide or oxalyl chloride.

The amidation is in general carried out in a temperature range from −20° C. to +80° C., preferably from −10° C. to 30° C., and at normal pressure.

In addition to the abovementioned bases, suitable bases for this are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formulae (IV) and (V).

Acid-binding agents which can be employed for the amidation are alkali metal or alkaline earth metal carbonates such as sodium carbonate or potassium carbonate, alkali metal or alkaline earth metal hydroxides such as, for example, sodium hydroxide or potassium hydroxide, or organic bases such as pyridine, triethylamine or N-methylpiperidine, or bicyclic amidines such as 1,5-diazabicyclo[3.4.0]-non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. Ledis, *J. Am. Chem. Soc.* 95, 875 (1973); F. E. Frerman et al., *J. Biol. Chem.* 258, 7087–7093 (1983) and N. B. Benoton, K. Kluroda, *Int. Pept. Prot. Res.* 187, 17, 197 (1981)].

The acid-binding agents and dehydrating reagents are in general employed in an amount from 0.5 to 3 mol, preferably from 1 to 1.5 mol, relative to 1 mol of the corresponding carboxylic acids.

The abovementioned derivatisation of the substituents A, R, D and E is in general carried out by methods known from the literature, in which, by way of example, the reduction of aldehydes or alkoxycarbonyl compounds to alcohols (a), the reduction of double bonds (b) and the alkylation (c) are intended to be illustrated by the following:

a) The reduction of alkoxycarbonyl compounds or aldehydes to the corresponding alcohols is in general carried out with hydrides, such as lithium aluminium hydride or sodium borohydride, preferably with lithium aluminium hydride in inert solvents such as ethers, hydrocarbons or alcohols or their mixtures, preferably in ethers such as, for example, diethyl ether, tetrahydrofuran or dioxane, or alcohols such as ethanol, in the case of the aldehydes preferably with sodium borohydride in ethanol, in a temperature range from 0° C. to +150° C., preferably from +20° C. to +100° C., at normal pressure.

The reduction of a double bond is in general carried out by hydrogenation with hydrogen in the presence of a catalyst such as, for example, platinum or platinum oxides, rhodium, ruthenium, chlorotris(triphenylphosphine)rhodium, or palladium on animal carbon, preferably using palladium on animal carbon in a temperature range from 0° C. to +150° C., preferably from +25° C. to +100° C.

b) Suitable solvents for the hydrogenation are protic solvents such as, for example, methanol, ethanol and/or aprotic solvents such as, for example, tetrahydrofuran, toluene, dimethylformamide, methylene chloride, dioxane or ethyl acetate.

The hydrogenation is carried out at a pressure of 1 to 300 atm, preferably at 1 to 20 atm.

c) The alkylation is in general carried out in one of the abovementioned solvents using alkylating agents such as, for example, ($C_1$–$C_8$)-alkyl halides, sulphonic acid esters or substituted or unsubstituted ($C_1$–$C_6$)-dialkyl or ($C_1$–$C_{10}$)-diaryl sulphates, preferably methyl iodide, p-toluenesulphonic acid ester or dimethyl sulphate.

The compounds of the general formula (II) are known in some cases and can be prepared, for example, by alkylating compounds of the general formula (VI)

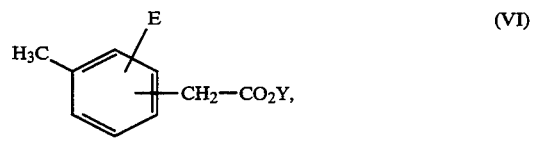

in which

E and Y have the abovementioned meaning, first with compounds of the general formula (VII)

L–Z              (VII)

in which

L has the abovementioned meaning and
Z represents halogen, preferably bromine,
in inert solvents, if appropriate in the presence of a base,
and in a second step a bromination is carried out on the methyl group by a customary method, if appropriate in the presence of a catalyst.

The alkylation is in general carried out in one of the abovementioned solvents, preferably in dimethylformamide in a temperature range from 0° C. to +70° C., preferably from 0° C. to +30° C., and at normal pressure.

A suitable starter (catalyst) for the bromination is, for example, azobisisobutyronitrile, dibenzoyl peroxide, preferably azobisisobutyronitrile, the starter being employed in an amount from 0.01 mol to 0.1 mol, preferably from 0.01 mol to 0.05 mol, relative to 1 mol of the compound of the general formula (VI).

The compounds of the general formula (VI) are known per se or can be prepared by known methods [cf. J. Chem. Soc., Perkin Trans. 1, (9), 1706–1707; J. Chem. Soc., Chem. Commun., (2), 167–168].

The compounds of the general formula (VII) are known per se [cf. Beilstein 5, 19/5, 24/5, 29] or can be prepared from the corresponding alcohols or cycloalkenes according to a customary method.

The compounds of the general formula (III) are likewise known per se [cf. for example Beilstein 25, 163; 23, 45; U.S. Pat. No. 4,355,040] or can be prepared according to a customary method.

As actual substance representatives, the compounds of the general formula (IV) are new and can be prepared by the abovementioned processes.

The amines of the general formula (V) are known or can be prepared by known processes [cf., for example, Beilstein 11/104, R. V. Vitzgert, Uspekhi, Khimii 32, 3 (1963); Russian Chem. Rev. 32, 1 (1963); Beilstein 4, 87].

The compounds of the general formula (I) according to the invention exhibit an unforeseeable, useful spectrum of pharmacological action.

The compounds according to the invention have a specific A-II antagonistic action, as they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, disorders of cerebral function, ischaemic brain diseases, peripheral circulatory disorders, functional disorders of the kidney and adrenal gland, bronchospastic and vascular diseases of the airways, sodium retention and oedemas.

Investigation of the Inhibition of the Contraction Induced by Agonists

Rabbits of either sex are stunned by a blow to the neck and bled out, or occasionally anaesthetised with Nembutal (about 60–80 mg/kg i.v.) and sacrificed by opening the thorax. The thorax aorta is removed, freed from adhering connective tissue, divided into ring segments 1.5 mm wide and individually transferred under an initial loading of about 3.5 g into 10 ml organ baths containing 5% carbon dioxide 95% oxygen-gassed Krebs-Henseleit nutrient solution temperature-controlled at 37° C. of the following composition: 119 mmol/l of NaCl; 2.5 mmol/l of $CaCl_2 \times 2\ H_2O$; 1.2 mmol/l of $KH_2PO_4$; 10 mmol/l of glucose; 4.8 mmol/l of KCl; 1.4 mmol/l of $MgSO_4 \times 7\ H_2O$ and 25 mmol/l of $NaHCO_3$.

The contractions are determined isometrically by means of Statham UC2 cells via bridge amplifiers (ifd Mülheim or DSM Aalen) and digitalised and evaluated by means of A/D converters (System 570, Keithley Munich). The agonist dose-response curves (DRC) are carried out hourly. With each DRC, 3 or 4 individual concentrations are applied to the baths at 4 min intervals. After completion of the DRC and the following washing-out cycles (16 times in each case for about 5 sec/min with the abovementioned nutrient solution), a stirring or incubation phase of 28 minutes follows, in the course of which the contractions as a rule reach the starting value again.

The height of the 3rd DRC in the normal case is used as a reference quantity for the evaluation of the test substance to be investigated in further runs, which test substance is applied to the baths in the following DRCs in an increasing dosage in each case at the start of the incubation time. Each aorta ring is in this case always stimulated for the whole day with the same agonists.

Agonists and their Standard Concentrations
(Application Volume per Individual Dose=100 μl)

| | | |
|---|---|---|
| KCl | 22.7; 32.7; 42.7; 52.7 | mmol/l |
| l-Noradrenaline | $3 \times 10^{-9}; 3 \times 10^{-8}; 3 \times 10^{-7}; 3 \times 10^{-6}$ | g/ml |
| Serotonin | $10^{-8}; 10^{-7}; 10^{-6}; 10^{-5}$ | g/ml |
| B-HT 920 | $10^{-7}; 10^{-6}; 10^{-5}$ | g/ml |
| Methoxamine | $10^{-7}; 10^{-6}; 10^{-5}$ | g/ml |
| Angiotensin II | $3 \times 10^{-9}; 10^{-8}; 3 \times 10^{-8}; 10^{-7}$ | g/ml |

To calculate the $IC_{50}$ (the concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only inhibited weakly at high concentrations.

TABLE A

Inhibition of the vascular concentration of isolated
aorta rings of rabbits in vitro
$IC_{50}$ (mol/l) against contractions induced by AII

| Ex. No.: | $IC_{50}$ [nM] |
|---|---|
| 7 | 5400 |
| 20 | 240 |

Blood Pressure Measurements on the Angiotensin II-infused Rat

Male Wistar rats (Moellegaard, Copenhagen, Denmark) having a body weight of 300–350 g are anaesthetised with Thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglion blocker pentolinium (5 mg/kg i.v.), the angiotensin II infusion is started (0.3 μg/kg/min). As soon as the blood pressure values have reached a stable plateau, the test substances are administered either intravenously or as a suspension or solution in 0.5% Tylose. The blood pressure changes under the effect of the substance are given in the table as average values ± SEM.

Determination of Anti-hypertensive Activity in Conscious Hypertensive Rats

The oral antihypertensive activity of the compounds according to the invention was tested on conscious rats having a surgically induced unilateral renal artery stenosis. To do this, the right renal artery was constricted with a silver clip of 0.18 mm internal width. In this type of hypertension, the plasma renin activity increases in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

Additionally, the compounds according to the invention inhibit the specific binding of radioactive angiotensin II in a concentration-dependent manner.

Interaction of the Compounds According to the Invention with the Angiotensin II Receptor on Membrane Fractions of the Adrenal Cortex (Cattle)

Adrenal cortices of cattle (ACs), which have been freshly removed and carefully freed from the gland medulla are comminuted in sucrose solution (0.32M) with the aid of an Ultra-Turrax (Janke & Kunkel, Staufen i.B.) to give a coarse membrane homogenate and partially purified in two centrifugation steps to give membrane fractions.

The investigations of receptor binding are carried out on partially purified membrane fractions of bovine ACs using radioactive angiotensin II in an assay volume of 0.25 ml which in particular contains the partially purified membranes (50–80 μg), $^3$H-angiotensin II (3–5 nM), test buffer solution (50 mM tris, pH 7.2, 5 mM $MgCl_2$, 0.25% BSA) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ and/or $IC_{50}$ values ($K_i$: $IC_{50}$ values corrected for the radioactivity used; $IC_{50}$ values: concentration at which the substance to be investigated causes a 50% inhibition of the specific binding of the radioligand).

$K_i=320$ nM   Ex. 7

$K_i=380$ nM   Ex. 13

Investigation of the Inhibition of Proliferation of Smooth Muscle Cells by the Compounds According to the Invention To determine the antiproliferative action of the compounds, smooth muscle cells are used which have been obtained from rats' aortas by means of media explant technique [R. Ross, J. Cell. Biol. 50. 172, 1971]. The cells are inoculated in suitable culture dishes, as a rule 96-hole plates, and cultured for 2–3 days in medium 199 containing 7.5% of FCS and 7.5% NCS, 2 mM of L-glutamine and 15 mM of HEPES. pH 7.4, in 5% $CO_2$ at 37° C. The cells are then synchronised for 2–3 days by serum starvation, and growth subsequently encouraged by serum or other factors. Test compounds are added simultaneously. After 16–20 hours, 1 μCi of $^3$H-thymidine is added and after a further 4 hours the incorporation of this substance into the TCA-precipitable DNA of the cells is determined.

To determine the halfmaximal inhibition of thymidine incorporation ($IC_{50}$) caused by addition of 10% FCS, the compounds were sequentially diluted in the range of $10^{-6}$M to $10^{-9}$M.

$IC_{50}=32$ nM   Ex. 29

$IC_{50}=6,7$ nM   Ex. 30

The new active compounds can be converted in the known manner into the customary formulations such as tablets, coated tablets, pills, granules, aerosols, syrups, emulsions, suspensions and solutions, using inert, nontoxic, pharmaceutically acceptable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it optionally being possible to use organic solvents as auxiliary solvents, for example in the case of the use of water as a diluent.

Administration is carried out in a customary manner, preferably orally or parenterally, in particular perlingually or intravenously.

In the case of parenteral use, solutions of the active compound can be employed using suitable liquid excipient materials.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg, of body weight.

In spite of this, it may be necessary to depart from the amounts mentioned, in particular depending on the body weight or the type of application route, on individual behaviour toward the medicament, or the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

Starting Compounds

EXAMPLE I tert-Butyl 4-methylphenylacetate

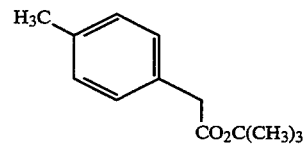

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2N hydrochloric acid and water. The organic phase is concentrated and distilled. Yield: 408 g (66% of theory) Boiling point: 73°–78° C./0.2 mm

EXAMPLE II tert-Butyl 2-cyclopentyl-2-(4-methylphenyl)acetate

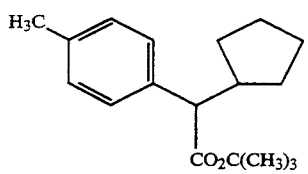

33.5 g (0.3 mol) of potassium tert-butoxide are initially introduced into 100 ml of DMF at 0° C. with exclusion of moisture, and 51.6 g (0.25 mol) of tert-butyl 4-methylphenylacetate in 250 ml of DMF are added dropwise. The mixture is stirred at 0° C. for 30 min and 32.2 ml (0.3 mol) of cyclopentyl bromide in 150 ml of DMF are added dropwise at 5°–15° C. and the mixture is stirred at 25° C. for 20 h. After concentration, the residue is partitioned between water/diethyl ether, and the ether phase is dried over sodium sulphate and concentrated. The product crystallises out. Yield: 67 g (97.5% of theory) Solidification point: 51°–53° C.

EXAMPLE III tert-Butyl 2-(4-bromomethyl-phenyl)-2-cyclopentyl-acetate

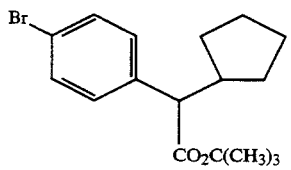

27.4 g (0.1 mol) of tert-butyl 2-cyclopentyl-2-(4-methyl-phenyl)-acetate are dissolved in 200 ml of carbon tetrachloride and the solution is heated to boiling. After addition of 0.82 g of azobisisobutyronitrile, 18.7 g (0.105 mol) of N-bromosuccinimide are added in portions and the mixture is then refluxed for 1 h, cooled to 0° C. and filtered off from the succinimide. After concentration of the filtrate the product precipitates. It is washed with petroleum ether (40:60) and dried. Yield: 20 g (57% of theory) Solidification point 73°–76° C.

EXAMPLE IV tert-Butyl 2-[4-(2-butyl-4-chloro-5-formyl-imidazol-1-yl-methyl)-phenyl]-2-cyclopentylacetate

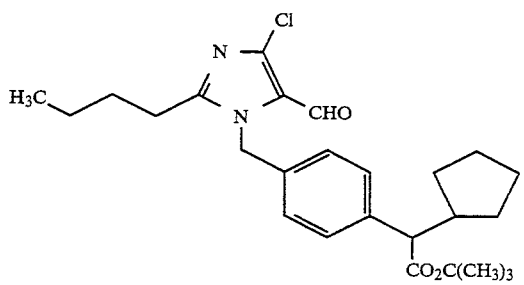

Under protective gas, 1.6 g (0.053 mol) of sodium hydride (80% strength) are suspended in 50 ml of DMF, 10 g (0.053 mol) of 2-butyl-5-formyl-4-chloroimidazole (preparation according to EP 324,377) in 100 ml of DMF are added dropwise at 0° C., then the mixture is stirred at 0° C. for 15 min and 18.9 g (0.053 mol) of tertbutyl 2-(4-bromomethylphenyl)-2-cyclopentylacetate in 100 ml of DMF are added dropwise. The mixture is stirred for 2 h at 0° C., the solvent is evaporated, the residue is taken up in diethyl ether, the solid is filtered off and, after concentration, the residue is chromatographed on silica gel 60 using dichloromethane. Yield: 16.2 g (66.7% of theory) Solidification point: 101°–102° C.

EXAMPLE V

2-[4-(2-Butyl-4-chloro-5-formyl-imidazol-1-yl-methyl)-phenyl]-2-cyclopentyl-acetic acid

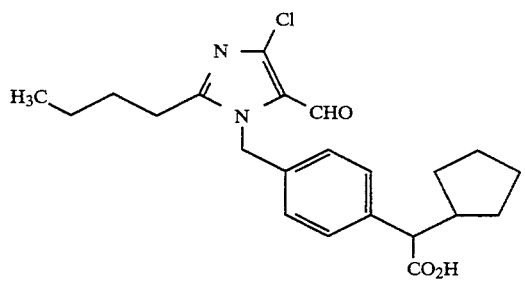

2.3 g (5 mmol) of the compound from Example IV are stirred for 5 h at 25° C. in 5 ml of dichloromethane and 5 ml of trifluoroacetic acid. After concentration, the crude product is chromatographed on silica gel 60 using dichloromethane/methanol (100:5). Yield: 1.8 g (87.6% of theory) Solidification point: 95°–98° C.

PREPARATION EXAMPLES

Example 1

N-(1-[Benzo[b]dioxol-5-yl]-2-hydroxy-propyl)-2-[4-(2-butyl-4-chloro-5-formyl-imidazol-1-yl-methyl)phenyl]-2-cyclopentylacetamide

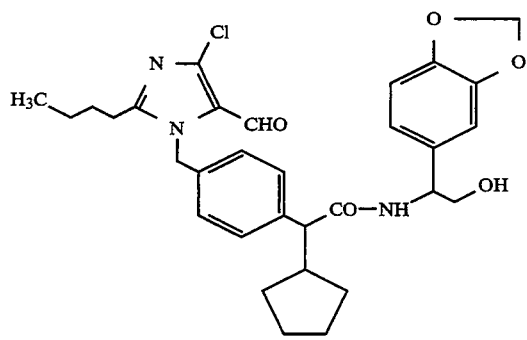

1.00 g (2.5 mmol) of the compound from Example V is dissolved in 30 ml of THF p.a. and treated at −30° C. with 0.70 ml (5.0 mmol) of triethylamine and 0.21 ml (2.75 mmol) of methanesulphonyl chloride and the mixture is stirred for 30 min. After addition of 305 mg (2.5 mmol) of 4-(N,N-dimethyl-amino)-pyridine and 544 mg (3.0 mmol) of 5-(1-amino-2-hydroxy-ethyl)-benzo[b]dioxolane in 10 ml of THF p.a., the mixture is stirred for 20 hours at 23° C., then treated with 35 ml of water, 0.4 ml of acetic acid and 35 ml of ethyl acetate, and the phases are separated and neutralised 3 times using 34 ml of ethyl acetate each time. The combined organic phases are dried using sodium sulphate and evaporated, and the residue obtained is chromatographed on silica gel 60 (Merck, petroleum ether/ethyl acetate first 2:1 later 1:1). Yield: 572 mg (1.0 mmol) $R_f$=0.24 (petroleum ether/ethyl acetate 1:1)

Example 2

1-L-Phenethyl-2-[4-(2-butyl-4-chloro-5-formyl-imidazol-1-yl-methyl)phenyl]-2-cyclopentyl-acetamide

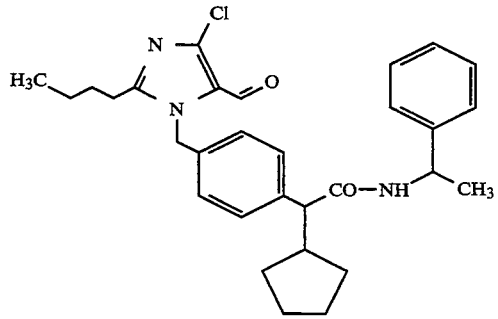

1 g of 2-[4-(2-butyl-4-chloro)-5-formyl-imidazol-1-yl-methyl)-phenyl]-2-cyclopentyl-acetic acid is treated with stirring at room temperature in 20 ml of dichloromethane with 574 mg of 1-hydroxy-benzotriazole and then after cooling to 0° C. with 773 mg of dicyclohexyl-carbodiimide. The mixture is rendered alkaline with triethylamine and a solution of 365 mg of L-phenethylamine in 10 ml of dichloromethane is added dropwise at 0° C. After one hour, the mixture is warmed to room temperature and stirred for a further 18 h. For working-up, it is extracted with water, the aqueous phase is shaken twice with dichloromethane, and the combined organic phases are dried over sodium sulphate, filtered, concentrated and chromatographed on 100 g of silica gel 60 using dichloromethane/methanol (98:2). Yield: 622 mg (49% of theory) $R_f$=0.94 (CH$_2$Cl$_2$/MeOH=9:1)

Example 3

1-L-phenethyl-2-[4-(2-butyl-4-chloro-5-hydroxymethyl-imidazol-1-yl-methyl)phenyl]-2-cyclopentyl-acetamide

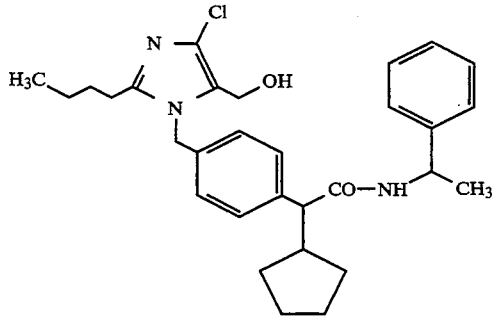

270 mg of the compound from Example 2 are treated at room temperature in 10 ml of ethanol with 20 mg of sodium borohydride and the mixture is stirred for 30 minutes. After treating with water, it is acidified with 1N acetic acid (pH 4–5) and extracted three times with ethyl acetate, and the combined organic phases are dried over sodium sulphate, filtered, concentrated and chromatographed on 7 g of silica gel 60 using ethyl acetate/petroleum ether 40–60 (7:3). Yield: 69 mg (27% of theory) $R_f$=0.73 (dichloromethane/methanol=9:1)

The compounds shown in Tables 1, 2 and 3 are prepared in analogy to the procedures of Examples 1, 2 and 3:

TABLE 1

| Example No. | D | R$^2$ | R$_f$/solvent | Isomer |
|---|---|---|---|---|
| 4 | —CHO | (tetrahydrofuran-2-yl) | 0.28$^A$ | 2 dia/ent |
| 5 | —CHO | (tetrahydrofuran-2-yl) | 0.28$^A$ | 2 dia/ent |
| 6 | —CH$_2$OH | (tetrahydrofuran-2-yl) | 0.31$^A$ | 2 dia/ent |

TABLE 1-continued

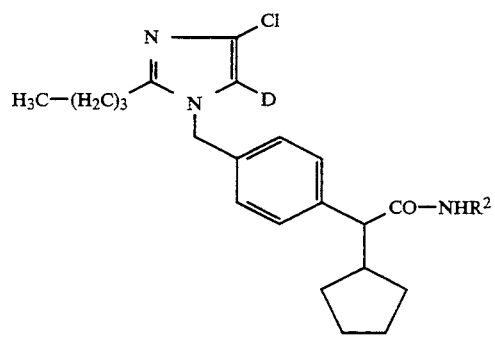

| Example No. | D | R² | Rf/solvent | Isomer |
|---|---|---|---|---|
| 7 | —CHO | 2-hydroxyphenyl-CH(CH₃)-CO₂CH₃ | 0.18[B] | 4 dia |
| 8 | —CHO | 2-hydroxyphenyl-CH(CH₃)-CO₂CH₃ | 0.18[B] | dia A/rac |
| 9 | —CH₂OH | 2-hydroxyphenyl-CH(CH₃)-CO₂CH₃ | 0.21[A] | 4 dia |
| 10 | —CH₂OH | 2-hydroxyphenyl-CH(CH₃)-CO₂CH₃ | 0.21[A] | dia A/rac |
| 11 | —CH₂OH | 2-hydroxyphenyl-CH(CH₃)-CO₂H | 0.48[C] | 4 dia |
| 12 | —CH₂OH | (3R)-tetrahydrofuran-3-yl | 0.31[A] | dia A/ent |
| 13 | —CH₂OH | (3R)-tetrahydrofuran-3-yl | 0.31[A] | 2 dia/ent |

TABLE 1-continued

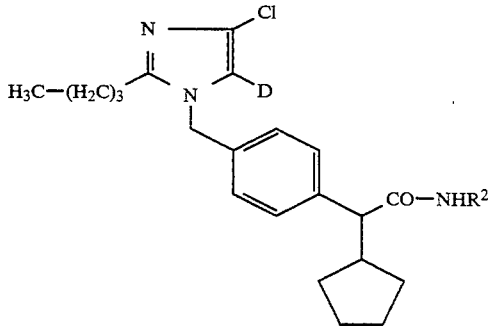

| Example No. | D | R² | Rf/solvent | Isomer |
|---|---|---|---|---|
| 14 | —CH₂OH | 3,4-methylenedioxyphenyl-CH(CH₃)-CH₂OH | 0.30[D] | dia A/rac |
| 15 | —CH₂OH | 3,4-methylenedioxyphenyl-CH(CH₃)-CH₂OH | 0.30[D] | dia B/rac |
| 16 | —CH₂OH | 3,4-methylenedioxyphenyl-CH(CH₃)-CH₂OH | 0.39/0.30[D] | 4 dia |

TABLE 2

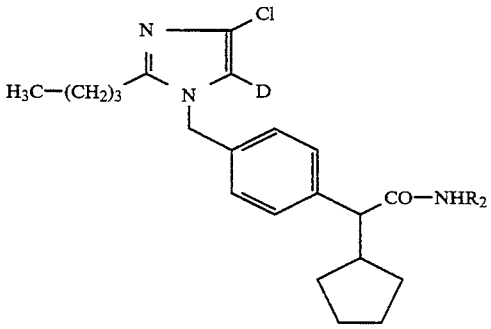

| Example No. | D | R² | Rf/solvent | Isomer |
|---|---|---|---|---|
| 17 | —CHO | C₆H₅–CH(CO₂CH₃)– (S) | 0.98[E] | 2 dia/ent |

TABLE 2-continued
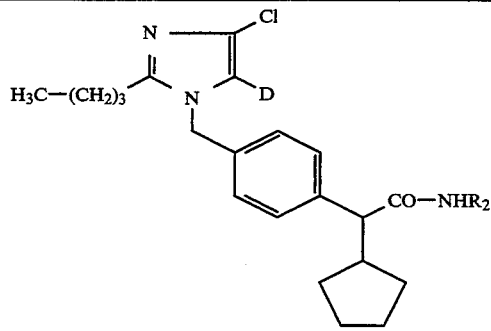
| Example No. | D | R² | Rf/solvent | Isomer |
|---|---|---|---|---|
| 18 | —CHO | C₆H₅, CO₂H (with iPr) | 0.18$^E$ | 2 dia/ent |
| 19 | —CH₂OH | C₆H₅, CO₂H (with iPr) | 0.32$^G$ | 2 dia/ent |
TABLE 3
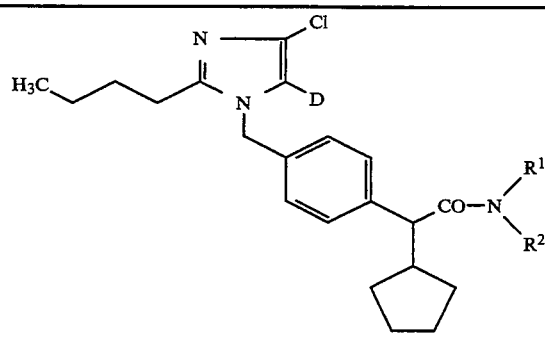
| Example No. | D | R¹ | R² | Rf/solvent | Isomer |
|---|---|---|---|---|---|
| 20 | | C₅H₁₁ / CO₂H alkenyl | 2-pyridyl-CH(CH₃)– | 0.44$^G$ | 4 dia |
| 21 | | C₅H₁₁ / CO₂CH₃ alkenyl | 2-pyridyl-CH(CH₃)– | 0.73$^H$ | 4 dia |
| 22 | CHO | H | sec-butylphenyl (PhCH(CH₃)CH₂CH₃) | 0.76 B | 4 dia |
| 23 | CHO | H | 2-pyridyl-CH(CH₃)-Ph | 0.85 I | 4 dia |
| 24 | CH₂OH | H | sec-butylphenyl | 0.50 I | 4 dia |

TABLE 3-continued
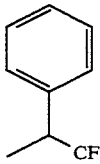
| Example No. | D | R¹ | R² | Rf/solvent | Isomer |
|---|---|---|---|---|---|
| 25 | CHO | H | 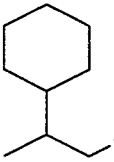 | 0.89 I | 4 dia |
| 26 | CHO | H | 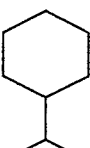 | 0.52 I | 4 dia |
| 27 | CHO | H | 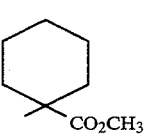 | 0.97 I | 4 dia |
| 28 | CHO | H | 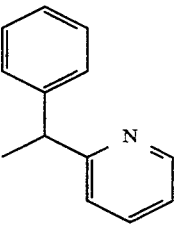 | 0.71 B | rac |
| 29 | $CH_2OH$ | H | 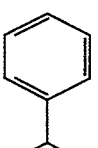 | 0.31 J | 4 dia |
| 30 | $CH_2OH$ | H | 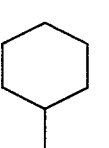 | 0.25 I | 4 dia |
| 31 | $CH_2OH$ | H | | 0.23 I | 4 dia |

TABLE 3-continued
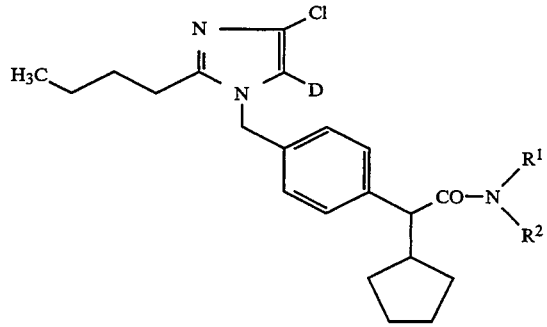
| Example No. | D | R¹ | R² | Rf/solvent | Isomer |
|---|---|---|---|---|---|
| 32 | CHO | H | 2-cyclohexyl-1-methyl-ethanol | 0.33 I | rac |
| 33 | CH₂OH | H | 2-cyclohexyl-1-methyl-ethanol | 0.27 J | rac |
| 34 | CHO | H | 1-phenyl-1-(pyridin-3-yl)ethyl | 0.13 B | 4 dia |
| 35 | CHO | H | 1-phenyl-1-(pyridin-4-yl)ethyl | 0.62 I | 4 dia |
| 36 | CH₂OH | H | 1-phenyl-1-(pyridin-3-yl)ethyl | 0.46 I | 4 dia |
| 37 | CH₂OH | H | 1-phenyl-1-(pyridin-4-yl)ethyl | 0.51 I | 4 dia |

TABLE 3-continued

| Example No. | D | R¹ | R² | $R_f$/solvent | Isomer |
|---|---|---|---|---|---|
| 38 | CHO | H | 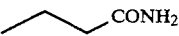 | 0.17 A | 2 dia/ent |
| 39 | CH₂OH | H |  | 0.58 C | 2 dia/ent |

*Mobile phase mixtures
A = petroleum ether:ethyl acetate 1:1
B = dichloromethane:methanol 50:1
C = dichloromethane:methanol 5:1
D = petroleum ether:ethyl acetate 1:4
E = dichloromethane:methanol 9:1
F = petroleum ether:ethyl acetate 7:3
G = dichloromethane:methanol:glacial acetic acid 9:1:0.1
H = petroleum ether:ethyl acetate = 1:2
I = dichloromethane:methanol = 10:1
J = dichloromethane:methanol = 20:1
Definition of the isomer types:
4dia = Mixture of the four possible diastereomers at two assymetric centres in the molecule
diaA/rac = Racemic diastereomer with the greater $R_f$ value
diaB/rac = Racemic diastereomer with the smaller $R_f$ value
diaA/ent = Diastereomer having the greater $R_f$ value (an enantiomer)
diaB/ent = Diastereomer having the smaller $R_f$ value (an enantiomer)
2dia/ent = Mixture of two enantiomerically pure diastereomers
rac = Racemate
ent = Enantiomer

We claim:
1. A substituted phenylacetamide of the formula

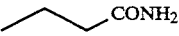

(I)

in which
A represents straight-chain or branched alkyl or alkenyl each having up to 8 carbon atoms, or represents cycloalkyl having 3 to 8 carbon atoms,
R represents hydrogen, halogen or perfluoroalkyl having up to 5 carbon atoms,
D represents a group of the formula —CH₂OR³, —CO—R⁴, —CO—NR⁵R⁶,

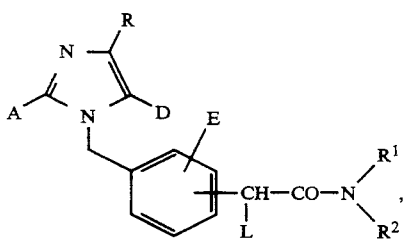 or 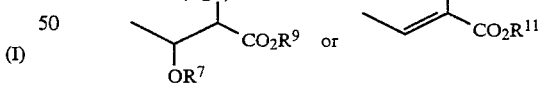

in which
R³ denotes hydrogen or straight-chain or branched alkyl having up to 8 carbon atoms,
R⁴ represents hydrogen, hydroxyl or straight-chain or branched alkoxy having up to 8 carbon atoms,
R⁵ and R⁶ are identical or different and denote hydrogen, straight-chain or branched alkyl having up to 8 carbon atoms, or
R⁵ has the abovementioned meaning and
R⁶ denotes a group of the formula —SO₂R¹², in which
R¹² denotes straight-chain or branched alkyl having up to 6 carbon atoms, or benzyl or phenyl which are optionally substituted by straight-chain or branched alkyl having up to 6 carbon atoms, a and b are identical or different and denote a number 0, 1 or 2, $R^7$ denotes hydrogen or straight-chain or branched alkyl having up to 8 carbon atoms or a hydroxyl protective group selected from the group consisting of trimethylsilyl, triethylsilyl, triisopropylsilyl, tert-butyldimethylsilyl, tert-butyldiphenylsilyl, trimethylsilylethoxycarbonyl, benzyl, triphenylmethyl(trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl, and methoxybenzoyl, $R^8$ and $R^{10}$ are identical or different and denote hydrogen, straight-chain or branched alkyl having up to 6 carbon atoms, cycloalkyl having 3 to 8 carbon atoms, phenyl or thienyl, $R^9$ and $R^{11}$ are identical or different and denote hydrogen or straight-chain or branched alkyl having up to 8 carbon atoms, E represents hydrogen, halogen, nitro, hydroxyl, trifluoromethyl, trifluoromethoxy, straight-chain or branched alkyl, alkoxy or alkoxycarbonyl each having up to 6 carbon atoms, cyano or carboxyl, L represents straight-chain or branched alkyl having up to 8 carbon atoms, which is optionally substituted by cycloalkyl having 3 to 8 carbon atoms or by phenyl, represents cycloalkyl having 3 to 12 carbon atoms, which is optionally substituted by straight-chain or branched alkyl having up to 6 carbon atoms, $R^1$ represents hydrogen or straight-chain or branched alkyl having up to 8 carbon atoms, $R^2$ represents pyridyl, morpholinyl, tetrahydropyranyl, tetrahydrofuranyl, quinolinyl, dihydrobenzopyranyl or dihydrobenzofuranyl, which is optionally substituted up to 3 times by identical or different substituents from the group consisting of nitro, cyano, halogen, hydroxyl, trifluoromethyl, carboxyl, straight-chain or branched alkoxy or alkoxycarbonyl each having up to 6 carbon atoms, phenoxy, benzyloxy, phenoxycarbonyl and benzyloxycarbonyl, or represents a radical of the formula

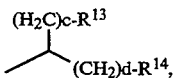

in which $R^{13}$ denotes phenyl which is optionally substituted up to 3 times by identical or different substituents from the group consisting of halogen, hydroxyl and trifluoromethyl or by straight-chain or branched alkyl or alkoxy each having up to 8 carbon atoms, c, d, e and f are identical or different and denote a number 0, 1, 2, 3 or 4, $R^{14}$ denotes hydrogen, trifluoromethyl, carboxyl or straight-chain or branched alkoxycarbonyl having up to 8 carbon atoms or the group —CO—NH$_2$ or pyridyl or morpholinyl, or a salt thereof.

2. A substituted phenylacetamide according to claim 1 in which

A represents straight-chain or branched alkyl or alkenyl each having up to 6 carbon atoms, or represents cyclopropyl, cyclobutyl, cyclopentyl, cyclohexyl or cycloheptyl, R represents hydrogen, fluorine, chlorine, bromine or perfluoroalkyl having up to 4 carbon atoms, represents a group of the formula —CH$_2$OR$^3$, —CO—R$^4$, —CO—NR$^5$R$^6$,

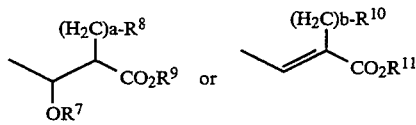

in which $R^3$ denotes hydrogen or straight-chain or branched alkyl having up to 6 carbon atoms, $R^4$ denotes hydrogen, hydroxyl or straight-chain or branched alkoxy having up to 6 carbon atoms, $R^5$ and $R^6$ are identical or different and denote hydrogen or straight-chain or branched alkyl having up to 6 carbon atoms, or $R^5$ has the abovementioned meaning and denotes a group of the formula —SO$_2$R$^{12}$, in which $R^{12}$ denotes straight-chain or branched alkyl having up to 4 carbon atoms, or benzyl or phenyl which are optionally substituted by straight-chain or branched alkyl having up to 4 carbon atoms, a and b are identical or different and denote a number 0 or 1, $R^7$ denotes hydrogen or straight-chain or branched alkyl having up to 6 carbon atoms or acetyl, $R^8$ and $R^{10}$ are identical or different and denote straight-chain or branched alkyl having up to 4 carbon atoms, cyclopropyl, cyclobutyl, cyclopentyl, cyclohexyl or cycloheptyl, phenyl or thienyl, $R^9$ and $R^{11}$ are identical or different and denote hydrogen or straight-chain or branched alkyl having up to 6 carbon atoms, E represents hydrogen, fluorine, chlorine, bromine, trifluoromethyl, carboxyl or straight-chain or branched alkyl, alkoxy or alkoxycarbonyl each having up to 4 carbon atoms, L represents straight-chain or branched alkyl having up to 6 carbon atoms, which is optionally substituted by cyclopropyl, cyclobutyl, cyclopentyl, cyclohexyl, cycloheptyl, cyclooctyl or phenyl, represents cyclopropyl, cyclobutyl, cyclopentyl, cyclohexyl, cycloheptyl or cyclooctyl which are optionally substituted by straight-chain or branched alkyl having up to 4 carbon atoms, $R^1$ represents hydrogen or straight-chain or branched alkyl having up to 6 carbon atoms, $R^2$ represents pyridyl, morpholinyl, tetrahydropyranyl, tetrahydrofuranyl, quinolinyl, dihydrobenzopyranyl or dihydrobenzofuranyl which are optionally substituted up to 2 times by identical or different substituents selected from the group consisting of nitro, cyano, fluorine, chlorine, bromine, hydroxyl, straight-chain or branched alkoxy having up to 4 carbon atoms, phenoxy and benzyloxy, or represents a radical of the formula

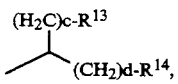

in which
- $R^{13}$ denotes phenyl which is optionally substituted up to 2 times by identical or different substituents from the group consisting of fluorine, chlorine, bromine, hydroxyl and trifluoromethyl or by straight-chain or branched alkyl or alkoxy each having up to 6 carbon atoms,
- c, d, e and f are identical or different and denote a number 0, 1, 2 or 3,
- $R^{14}$ denotes hydrogen, trifluoromethyl, carboxyl or straight-chain or branched alkoxycarbonyl having up to 6 carbon atoms or the group —CO—NH$_2$, pyridyl or morpholinyl, or a salt thereof.

3. A substituted phenylacetamide according to claim 1 in which
- A represents straight-chain or branched alkyl or alkenyl each having up to 4 carbon atoms, or represents cyclopropyl, cyclopentyl or cyclohexyl,
- R represents hydrogen, fluorine, chlorine or perfluoroalkyl having up to 2 carbon atoms,
- D represents a group of the formula —CH$_2$OR$^3$, —CO—R$^4$, —CO—NR$^5$R$^6$,

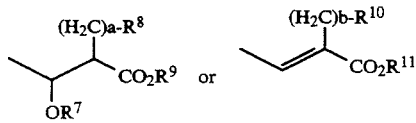

in which
- $R^3$ denotes hydrogen or straight-chain or branched alkyl having up to 4 carbon atoms,
- $R^4$ denotes hydrogen, hydroxyl or straight-chain or branched alkoxy having up to 4 carbon atoms,
- $R^5$ and $R^6$ are identical or different and denote hydrogen or straight-chain or branched alkyl having up to 4 carbon atoms, or
- $R^5$ has the abovementioned meaning and
- $R^6$ denotes a group of the formula —SO$_2$R$^{12}$, in which
- $R^{12}$ denotes methyl, ethyl, benzyl, p-tolyl or phenyl,
- a and b are identical or different and denote a number 0 or 1,
- $R^7$ denotes hydrogen or straight-chain or branched alkyl having up to 4 carbon atoms,
- $R^8$ and $R^{10}$ are identical or different and denote cyclopropyl, cyclohexyl or phenyl,
- $R^9$ and $R^{11}$ are identical or different and denote hydrogen or straight-chain or branched alkyl having up to 4 carbon atoms,

- E represents hydrogen, fluorine, chlorine, bromine, trifluoromethyl, trifluoromethoxy or methyl,
- L represents straight-chain or branched alkyl having up to 4 carbon atoms, which is optionally substituted by cyclopropyl, cyclopentyl, cyclohexyl, cycloheptyl or phenyl, represents cyclopropyl, cyclopentyl, cyclohexyl, cycloheptyl or cyclooctyl,
- $R^1$ represents hydrogen or straight-chain or branched alkyl having up to 4 carbon atoms,
- $R^2$ represents pyridyl, morpholinyl, tetrahydropyranyl or tetrahydrofuranyl, or represents a radical of the formula

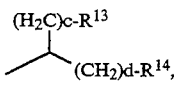

in which
- $R^{13}$ denotes phenyl which is optionally substituted by fluorine, hydroxyl, trifluoromethyl or by straight-chain or branched alkyl or alkoxy each having up to 4 carbon atoms or by methylenedioxy,
- c, d, e and f are identical or different and denote a number 0, 1 or 2,
- $R^{14}$ denotes hydrogen, trifluoromethyl, carboxyl or straight-chain or branched alkoxycarbonyl having up to 4 carbon atoms or the group —CO—NH$_2$ or pyridyl, or a salt thereof.

4. A compound according to claim 1 wherein such compound is N-(1-phenyl-1-pyrid-2-yl)methyl]-2-[4-(2-butyl-4-chloro-5-formyl-imidazol-1-yl-methyl)phenyl]-2-cyclopentyl-acetamide of the formula

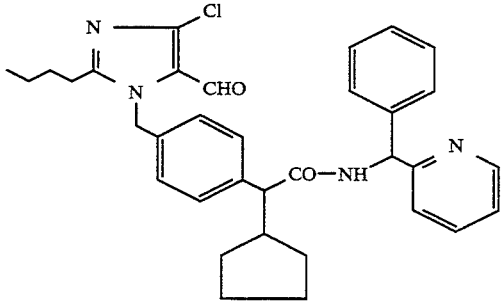

or a salt thereof.

5. A composition for the treatment of atriable hypertension and arteriosclerosis comprising an mount effective therefor of a compound or salt thereof according to claim 1 and a pharmacologically acceptable diluent.

6. The method of treating atriable hypertension and arteriosclerosis in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,352,687
DATED      : October 4, 1994
INVENTOR(S): Muller, et al.

It is certified that error appears in the above-indentified patent and that said Letters Patent is hereby corrected as shown below:

Col. 32, line 11    Before " represents " insert -- D --

Col. 32, line 29    Before " denotes " insert -- $R^6$ --

Signed and Sealed this

Twenty-third Day of January, 1996

Attest:

BRUCE LEHMAN

Attesting Officer       Commissioner of Patents and Trademarks